US009616238B2

(12) United States Patent
Demmer et al.

(10) Patent No.: US 9,616,238 B2
(45) Date of Patent: Apr. 11, 2017

(54) METHOD AND APPARATUS FOR DETERMINING LONGEVITY

(71) Applicant: Medtronic, Inc., Minneapolis, MN (US)

(72) Inventors: Wade M Demmer, Coon Rapids, MN (US); James D Reinke, Maple Grove, MN (US); Todd J Sheldon, North Oaks, MN (US); Eric R Williams, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 307 days.

(21) Appl. No.: 14/256,133

(22) Filed: Apr. 18, 2014

(65) Prior Publication Data

US 2015/0157866 A1 Jun. 11, 2015

Related U.S. Application Data

(60) Provisional application No. 61/912,216, filed on Dec. 5, 2013.

(51) Int. Cl.
*H02J 7/00* (2006.01)
*A61N 1/37* (2006.01)
*G01R 31/36* (2006.01)
*A61N 1/362* (2006.01)
*H01M 10/48* (2006.01)

(52) U.S. Cl.
CPC .......... *A61N 1/3708* (2013.01); *A61N 1/362* (2013.01); *G01R 31/3606* (2013.01); *G01R 31/3648* (2013.01); *G01R 31/3679* (2013.01); *H01M 10/48* (2013.01)

(58) Field of Classification Search
CPC ..... A61N 1/326; A61N 1/3708; H01M 10/48; G01R 31/3606; G01R 31/3648; G01R 31/3679
USPC ............................. 320/145; 607/29
See application file for complete search history.

(56) References Cited

U.S. PATENT DOCUMENTS

| 5,458,624 | A | 10/1995 | Renirie et al. |
| 5,620,474 | A | 4/1997 | Koopman |
| 6,108,579 | A | 8/2000 | Snell et al. |
| 6,185,461 | B1 | 2/2001 | Er |
| 6,648,823 | B2 | 11/2003 | Thompson |

(Continued)

OTHER PUBLICATIONS (PCT/US2014/067229) PCT Notification of Transmittal of the International Search Report and the Written Opinion of the International Searching Authority.

*Primary Examiner* — Nathaniel Pelton
(74) *Attorney, Agent, or Firm* — Carol F. Barry

(57) ABSTRACT

A method and apparatus for determining estimated remaining longevity for an implantable stimulator. The device employs pre-calculated numbers of days for various combinations conditions of device usage parameters to determine remaining device longevity based upon identified actual conditions of device usage and employs the determined longevity to change longevity indicator states in the device. While between longevity state changes, the device the identified conditions of device usage and adjusts the determined longevity if the conditions of use change significantly. The indicator states may correspond to one or more of Recommended Replacement Time (RRT), Elective Replacement Indicator (ERI) or End of Service (EOS).

25 Claims, 10 Drawing Sheets

(56) References Cited

U.S. PATENT DOCUMENTS

| | | |
|---|---|---|
| 6,671,522 B1 | 12/2003 | Beaudou |
| 7,565,195 B1 | 7/2009 | Kroll et al. |
| 7,620,452 B1 | 11/2009 | Russie |
| 8,090,566 B2 | 1/2012 | Brown |
| 8,209,010 B2 | 6/2012 | Ryu et al. |
| 8,401,646 B2 | 3/2013 | Stadler et al. |
| 8,417,338 B2 | 4/2013 | Rogers et al. |
| 8,452,395 B2 | 5/2013 | Crespi |
| 8,612,167 B2 | 12/2013 | Schmidt et al. |
| 2004/0039424 A1 | 2/2004 | Merritt et al. |
| 2004/0162592 A1* | 8/2004 | Betzold ............... A61N 1/3708 607/27 |
| 2005/0177206 A1 | 8/2005 | North et al. |
| 2005/0277994 A1 | 12/2005 | McNamee et al. |
| 2007/0179549 A1* | 8/2007 | Russie ............... A61N 1/3708 607/29 |
| 2008/0306569 A1 | 12/2008 | Tobacman |
| 2009/0182517 A1 | 7/2009 | Gandhi et al. |
| 2010/0010559 A1 | 1/2010 | Zhang et al. |
| 2011/0208455 A1 | 8/2011 | Tobacman |
| 2012/0010672 A1 | 1/2012 | Crespi |
| 2012/0010673 A1 | 1/2012 | Bowers |
| 2012/0101546 A1* | 4/2012 | Stadler ............... A61N 1/3712 607/28 |
| 2012/0109248 A1 | 5/2012 | Danielsson et al. |
| 2012/0109259 A1 | 5/2012 | Bond et al. |

* cited by examiner

FIG. 10

| Pulse Width = 0.09 ms | 0V-0.5V | >0.5V-0.75V | >0.75V-1V | >1V-1.25V | >1.25V-1.5V | >1.5V-1.75V | >1.75V-2V | >2V-2.25V | >2.25V-2.5V | >2.5V-3V | >3V-3.5V | >3.5V-4V | >4V-4.5V | >4.5V-5V |
|---|---|---|---|---|---|---|---|---|---|---|---|---|---|---|
| Pacing Percentage >75-100% | 1020 | 990 | 950 | 880 | 850 | 750 | 720 | 690 | 590 | 550 | 400 | 370 | 330 | 230 |
| >50-75% | 1030 | 1010 | 970 | 920 | 890 | 800 | 780 | 750 | 660 | 620 | 470 | 440 | 400 | 290 |
| >25-50% | 1040 | 1020 | 1000 | 960 | 940 | 870 | 850 | 830 | 750 | 710 | 570 | 540 | 500 | 380 |
| 0-25% | 1050 | 1040 | 1020 | 1000 | 990 | 950 | 930 | 920 | 870 | 840 | 730 | 700 | 670 | 550 |

| Pulse Width = 0.15 ms | 0V-0.5V | >0.5V-0.75V | >0.75V-1V | >1V-1.25V | >1.25V-1.5V | >1.5V-1.75V | >1.75V-2V | >2V-2.25V | >2.25V-2.5V | >2.5V-3V | >3V-3.5V | >3.5V-4V | >4V-4.5V | >4.5V-5V |
|---|---|---|---|---|---|---|---|---|---|---|---|---|---|---|
| Pacing Percentage >75-100% | 1000 | 950 | 890 | 810 | 760 | 640 | 600 | 570 | 470 | 420 | 290 | 260 | 240 | 160 |
| >50-75% | 1010 | 980 | 930 | 850 | 820 | 710 | 670 | 640 | 540 | 490 | 350 | 320 | 290 | 200 |
| >25-50% | 1030 | 1000 | 970 | 910 | 880 | 790 | 760 | 730 | 650 | 600 | 450 | 420 | 380 | 270 |
| 0-25% | 1040 | 1030 | 1010 | 970 | 960 | 900 | 880 | 860 | 790 | 760 | 620 | 590 | 550 | 430 |

| Pulse Width = 0.15 ms | 0V-0.5V | >0.5V-0.75V | >0.75V-1V | >1V-1.25V | >1.25V-1.5V | >1.5V-1.75V | >1.75V-2V | >2V-2.25V | >2.25V-2.5V | >2.5V-3V | >3V-3.5V | >3.5V-4V | >4V-4.5V | >4.5V-5V |
|---|---|---|---|---|---|---|---|---|---|---|---|---|---|---|
| Pacing Percentage >75-100% | 970 | 900 | 820 | 710 | 660 | 520 | 490 | 450 | 360 | 320 | 210 | 190 | 160 | 110 |
| >50-75% | 990 | 940 | 870 | 770 | 730 | 600 | 560 | 530 | 430 | 380 | 260 | 230 | 210 | 140 |
| >25-50% | 1010 | 970 | 920 | 850 | 810 | 700 | 660 | 630 | 530 | 480 | 350 | 320 | 280 | 190 |
| 0-25% | 1030 | 1010 | 980 | 940 | 910 | 830 | 810 | 780 | 700 | 660 | 510 | 480 | 440 | 330 |

| Pulse Width = 0.15 ms | 0V-0.5V | >0.5V-0.75V | >0.75V-1V | >1V-1.25V | >1.25V-1.5V | >1.5V-1.75V | >1.75V-2V | >2V-2.25V | >2.25V-2.5V | >2.5V-3V | >3V-3.5V | >3.5V-4V | >4V-4.5V | >4.5V-5V |
|---|---|---|---|---|---|---|---|---|---|---|---|---|---|---|
| Pacing Percentage >75-100% | 930 | 840 | 730 | 610 | 550 | 410 | 380 | 350 | 270 | 230 | 140 | 130 | 110 | 90 |
| >50-75% | 960 | 890 | 790 | 680 | 620 | 490 | 450 | 420 | 330 | 290 | 180 | 160 | 140 | 90 |
| >25-50% | 990 | 940 | 870 | 770 | 720 | 590 | 560 | 520 | 420 | 380 | 250 | 230 | 200 | 130 |
| 0-25% | 1020 | 990 | 950 | 890 | 850 | 750 | 730 | 690 | 600 | 550 | 410 | 380 | 340 | 240 |

| Pulse Width = 0.15 ms | 0V-0.5V | >0.5V-0.75V | >0.75V-1V | >1V-1.25V | >1.25V-1.5V | >1.5V-1.75V | >1.75V-2V | >2V-2.25V | >2.25V-2.5V | >2.5V-3V | >3V-3.5V | >3.5V-4V | >4V-4.5V | >4.5V-5V |
|---|---|---|---|---|---|---|---|---|---|---|---|---|---|---|
| Pacing Percentage >75-100% | 820 | 700 | 570 | 430 | 370 | 260 | 230 | 210 | 150 | 130 | 90 | 90 | 90 | 90 |
| >50-75% | 870 | 770 | 640 | 510 | 450 | 320 | 290 | 260 | 200 | 170 | 100 | 90 | 90 | 90 |
| >25-50% | 930 | 840 | 740 | 610 | 550 | 420 | 380 | 350 | 270 | 250 | 150 | 130 | 110 | 90 |
| 0-25% | 990 | 940 | 870 | 770 | 720 | 590 | 560 | 520 | 430 | 380 | 260 | 230 | 210 | 140 |

METHOD AND APPARATUS FOR DETERMINING LONGEVITY

CROSS-REFERENCE TO RELATED APPLICATIONS

This application claims the benefit of U.S. Provisional Application No. 61/912,216, filed on Dec. 5, 2013. The disclosure of the above application is incorporated herein by reference in its entirety.

TECHNICAL FIELD

This disclosure relates to implantable medical devices and, more particularly, to implantable medical devices.

BACKGROUND

A variety of medical devices for delivering a therapy and/or monitoring a physiological condition have been used clinically or proposed for clinical use in patients. Examples include medical devices that deliver therapy to and/or monitor conditions associated with the heart, muscle, nerve, brain, stomach or other organs or tissue. Some therapies include the delivery of electrical signals, e.g., stimulation, to such organs or tissues. Some medical devices may employ one or more elongated electrical leads carrying electrodes for the delivery of therapeutic electrical signals to such organs or tissues, electrodes for sensing intrinsic electrical signals within the patient, which may be generated by such organs or tissue, and/or other sensors for sensing physiological parameters of a patient. Some medical devices may be "leadless" and include one or more electrodes on an outer housing of the medical device to deliver therapeutic electrical signals to organs or tissues and/or sense intrinsic electrical signals or physiological parameters of a patient.

Medical leads may be configured to allow electrodes or other sensors to be positioned at desired locations for delivery of therapeutic electrical signals or sensing. For example, electrodes or sensors may be carried at a distal portion of a lead. A proximal portion of the lead may be coupled to a medical device housing, which may contain circuitry such as signal generation and/or sensing circuitry. In some cases, the medical leads and the medical device housing are implantable within the patient, while in other cases percutaneous leads may be implanted and connected to a medical device housing outside of the patient. Medical devices with a housing configured for implantation within the patient may be referred to as implantable medical devices. Leadless medical devices are typically implantable medical devices positioned within or adjacent to organs or tissues within a patient for delivery of therapeutic electrical signals or sensing. In some example, leadless implantable medical devices may be anchored to a wall of an organ or to tissue via a fixation mechanism.

Implantable cardiac pacemakers or cardioverter-defibrillators, for example, provide therapeutic electrical signals to the heart, e.g., via electrodes carried by one or more medical leads or via electrodes on an outer housing of a leadless implantable medical device. The therapeutic electrical signals may include pulses for pacing, or shocks for cardioversion or defibrillation. In some cases, a medical device may sense intrinsic depolarizations of the heart, and control delivery of therapeutic signals to the heart based on the sensed depolarizations. Upon detection of an abnormal rhythm, such as bradycardia, tachycardia or fibrillation, an appropriate therapeutic electrical signal or signals may be delivered to restore or maintain a more normal rhythm. For example, in some cases, an implantable medical device may deliver pacing stimulation to the heart of the patient upon detecting tachycardia or bradycardia, and deliver cardioversion or defibrillation shocks to the heart upon detecting fibrillation.

In general, implantable medical devices require a small housing form factor to enable an unobtrusive implantation within a patient. In the case of leadless implantable medical devices, the housing form factor must be extremely small to enable implantation within or adjacent to organs or tissue. For example, a leadless pacemaker may be implanted directly into a ventricle of the heart. Battery usage is always a concern when designing implantable medical devices, but this concern is increased for small form factor devices that can only accommodate a small battery canister.

SUMMARY

The details of one or more aspects of the disclosure are set forth in the accompanying drawings and the description below. Other features, objects, and advantages of the disclosure will be apparent from the description and drawings, and from the claims.

In traditional IPGs and ICDs, as a battery nears the end of its usable life, warnings are posted (RRT, ERI, EOS) and changes are made to a device's state (for example, at ERI the pacing mode and rate are changed to VVI 65 bpm). There are CENELAC specified minimum times between some of the state changes. Because of this, a combination of battery voltage/impedance trip points and a number of days at a state are used to advance these states. In some battery chemistries, the trip points occur on "plateaus" in the battery curve, making voltage/impedance an unreliable way to advance states. In this case, the number of days counters are the primary means of changing longevity states, with battery voltages as a backup only.

For leadless medical devices such as pacemakers, the amount of longevity is changed dramatically by the amount of pacing and the amplitude of pacing. For this reason, the present invention employs a dynamic mechanism to calculate the number of days between longevity states. The present invention employs pre-calculated numbers of days for various combinations of device use (for example, the device use the pacing amplitude and pulse width, then calculate the pacing percentage, and "look up" how many days of longevity are expected between given longevity states). In addition, while between states, the device monitors to verify that the device was still being used in the same way, and adjust the number of days remaining if the use changes significantly.

The invention employs pre-defined combinations of device use and remaining longevity to change longevity states in the device based on the device determined assessment of current device use and pre-calculated remaining longevity estimates.

Device battery life is extremely variable based on things like Pacing impedance, Pacing Amplitude, Pacing Pulse Width, Pacing Rate and Pacing Percentage. In the case of some devices, the battery is such that several of the longevity state switches occur during a battery voltage plateau. Changing longevity states at the right time is critical to providing the CENELAC required number of days between longevity states while also maximizing the device longevity. The invention is particularly beneficial in this context.

However, having the device constantly calculate exactly how much longevity is remaining is a burdensome level of complication. The present invention provides a balanced approach by having the device use device known parameters and a externally determined expected number of days between states for given conditions as a "look up table". This method in some cases can result in nearly half a year of additional longevity versus the standard method of longevity state change

Figure 8:
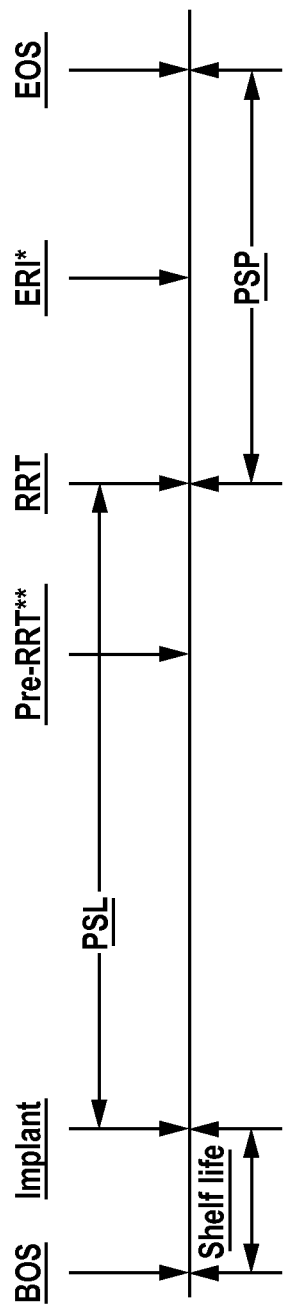

The inter-relation of defined events related to the invention is illustrated in FIG. 8.

Figure 9:
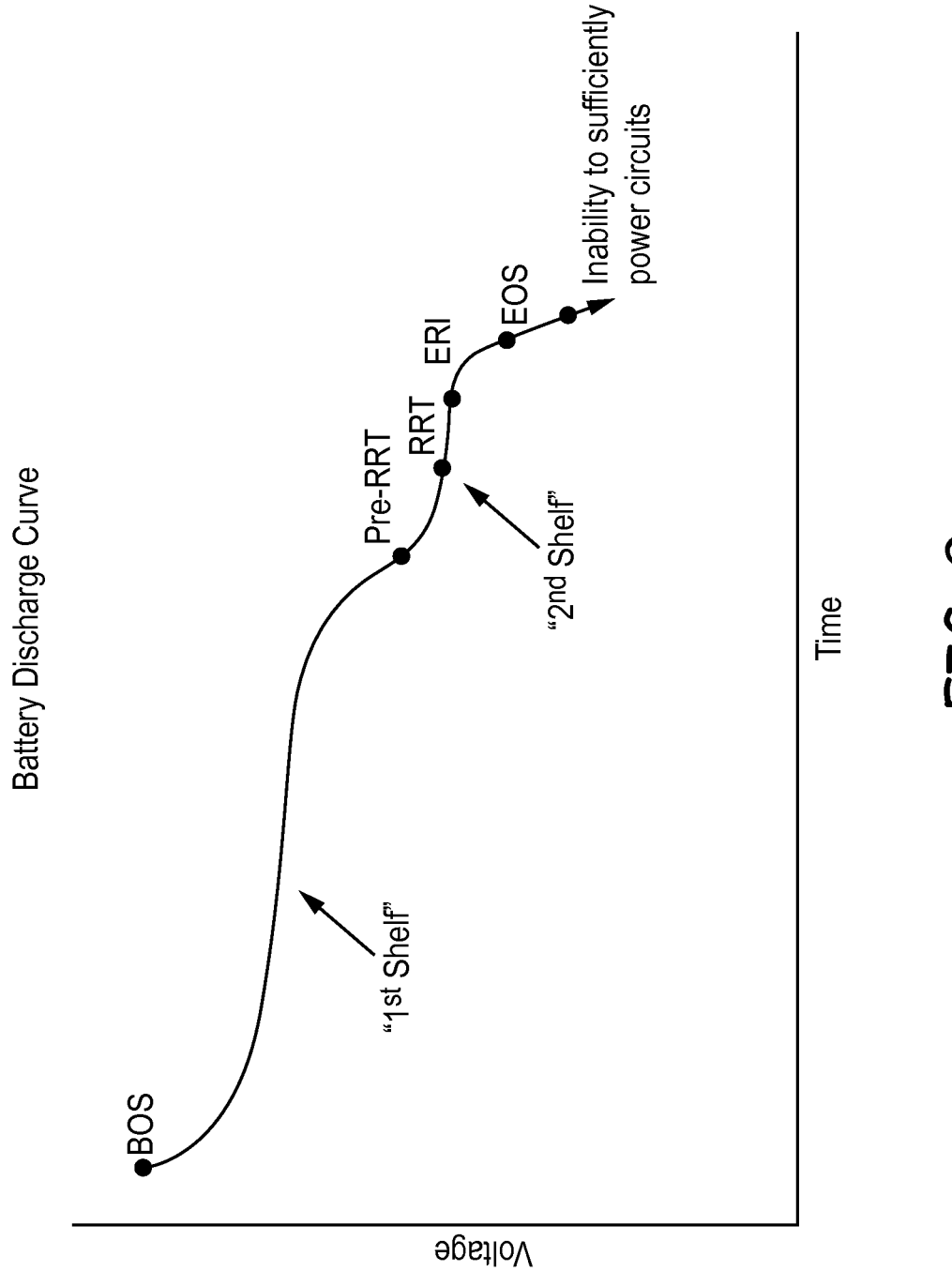

The times of occurrences of these defined events relative to an exemplary battery discharge curve is illustrated in FIG. 9

FIG. 10 is a table illustrating an exemplary mechanism by which the present invention calculates estimated remaining battery life (Remaining Longevity Duration Value) in days.

DETAILED DESCRIPTION

Figure 1:
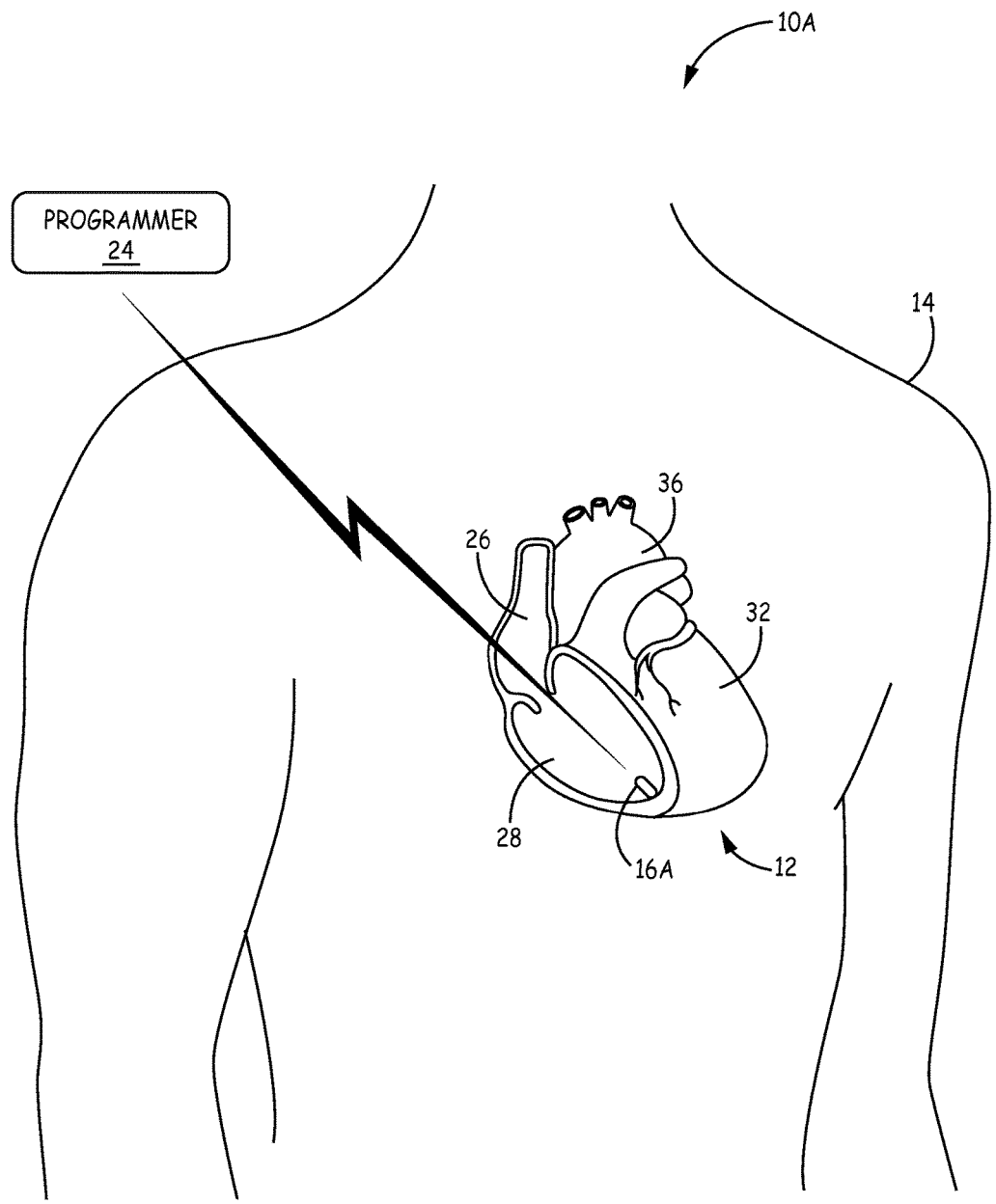
FIG. 1 is a diagram illustrating an example therapy system comprising a leadless implantable medical device (IMD) that may be used to monitor one or more physiological parameters of a patient and/or provide therapy to the heart of a patient.

FIG. 1 is a diagram illustrating an exemplary therapy system 10A that may be used to monitor one or more physiological parameters of patient 14 and/or to provide therapy to heart 12 of patient 14. Therapy system 10A includes an implantable medical device (IMD) 16A, which is coupled to programmer 24. IMD 16A may be an implantable leadless pacemaker that provides electrical signals to heart 12 via one or more electrodes (not shown in FIG. 1) on its outer housing. Additionally or alternatively, IMD 16A may sense electrical signals attendant to the depolarization and repolarization of heart 12 via electrodes on its outer housing. In some examples, IMD 16A provides pacing pulses to heart 12 based on the electrical signals sensed within heart 12. Patient 14 is ordinarily, but not necessarily, a human patient.

In the example of FIG. 1, IMD 16A is positioned wholly within heart 12 with one end proximate to the apex of right ventricle 28 to provide right ventricular (RV) pacing. Although IMD 16A is shown within heart 12 and proximate to the apex of right ventricle 28 in the example of FIG. 1, IMD 16A may be positioned at any other location outside or within heart 12. For example, IMD 16A may be positioned outside or within right atrium 26, left atrium 36, and/or left ventricle 32, e.g., to provide right atrial, left atrial, and left ventricular pacing, respectively. Depending in the location of implant, IMD 16A may include other stimulation functionalities. For example, IMD 16A may provide atrioventricular nodal stimulation, fat pad stimulation, vagal stimulation, or other types of neurostimulation. In other examples, IMD 16A may be a monitor that senses one or more parameters of heart 12 and may not provide any stimulation functionality. In some examples, system 10A may include a plurality of leadless IMDs 16A, e.g., to provide stimulation and/or sensing at a variety of locations.

FIG. 1 further depicts programmer 24 in communication with IMD 16A. In some examples, programmer 24 comprises a handheld computing device, computer workstation, or networked computing device. Programmer 24 includes a user interface that presents information to and receives input from a user. It should be noted that the user may also interact with programmer 24 remotely via a networked computing device.

A user, such as a physician, technician, surgeon, electrophysiologist, other clinician, or patient, interacts with programmer 24 to communicate with IMD 16A. For example, the user may interact with programmer 24 to retrieve physiological or diagnostic information from IMD 16A. A user may also interact with programmer 24 to program IMD 16A, e.g., select values for operational parameters of the IMD 16A. For example, the user may use programmer 24 to retrieve information from IMD 16A regarding the rhythm of heart 12, trends therein over time, or arrhythmic episodes.

As another example, the user may use programmer 24 to retrieve information from IMD 16A regarding other sensed physiological parameters of patient 14 or information derived from sensed physiological parameters, such intracardiac or intravascular pressure, activity, posture, respiration, tissue perfusion, heart sounds, cardiac electrogram (EGM), intracardiac impedance, or thoracic impedance. In some examples, the user may use programmer 24 to retrieve information from IMD 16A regarding the performance or integrity of IMD 16A or other components of system 10A, or a power source of IMD 16A. As another example, the user may interact with programmer 24 to program, e.g., select parameters for, therapies provided by IMD 16A, such as pacing and, optionally, neurostimulation.

IMD 16A and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16A implant site in order to improve the quality or security of communication between IMD 16A and programmer 24.

Figure 2:
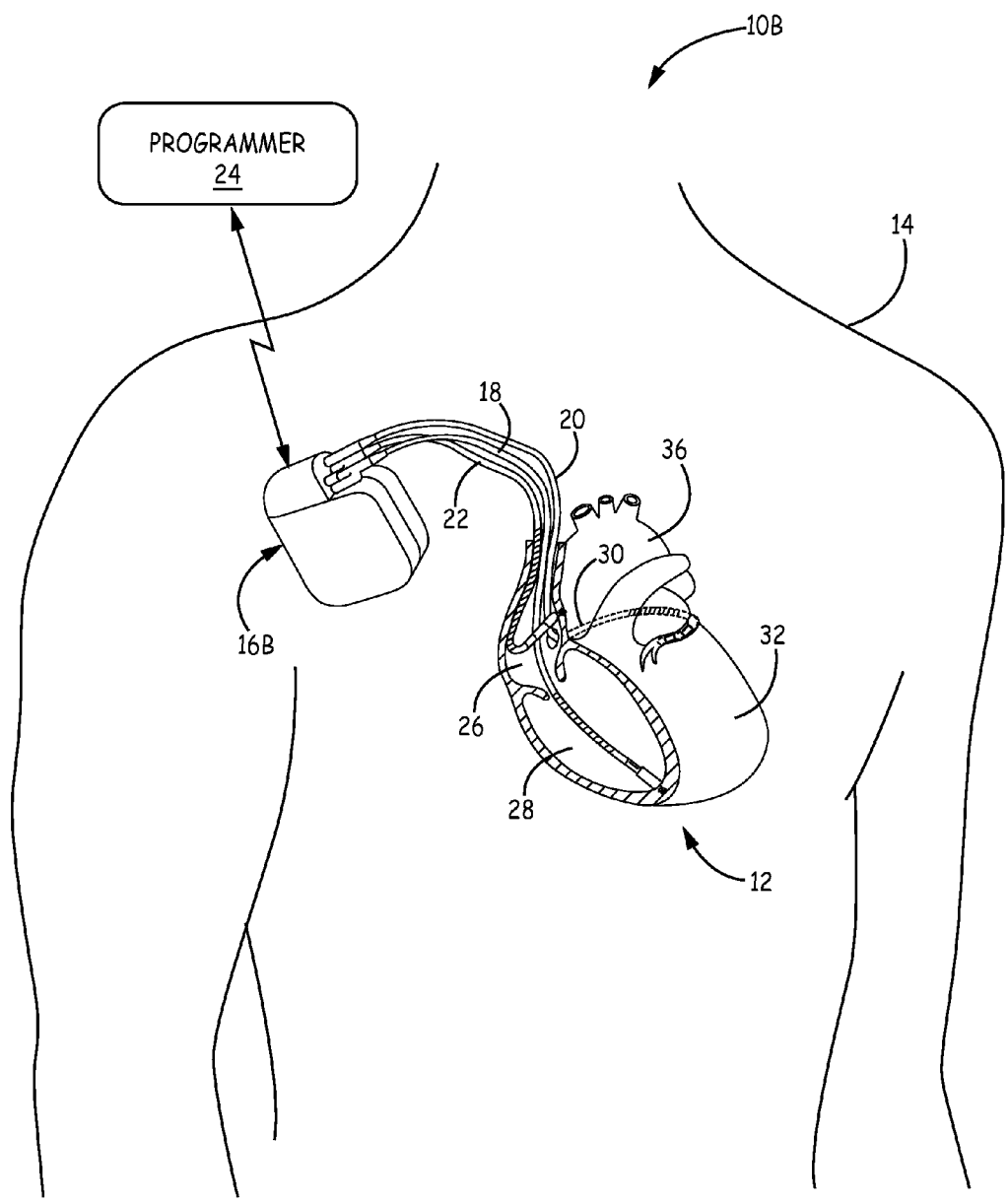
FIG. 2 is a diagram illustrating another example therapy system comprising an IMD coupled to a plurality of leads that may be used to monitor one or more physiological parameters of a patient and/or provide therapy to the heart of a patient.

FIG. 2 is a diagram illustrating another exemplary therapy system 10B that may be used to monitor one or more physiological parameters of patient 14 and/or to provide therapy to heart 12 of patient 14. Therapy system 10B includes IMD 16B, which is coupled to leads 18, 20, and 22, and programmer 24. In one example, IMD 16B may be an implantable pacemaker that provides electrical signals to heart 12 via electrodes coupled to one or more of leads 18, 20, and 22. In addition to pacing therapy, IMD 16B may deliver neurostimulation signals. In some examples, IMD 16B may also include cardioversion and/or defibrillation functionalities. In other examples, IMD 16B may not provide any stimulation functionalities and, instead, may be a dedicated monitoring device. Patient 14 is ordinarily, but not necessarily, a human patient.

Leads 18, 20, 22 extend into the heart 12 of patient 14 to sense electrical activity of heart 12 and/or deliver electrical stimulation to heart 12. In the example shown in FIG. 2, right ventricular (RV) lead 18 extends through one or more veins (not shown), the superior vena cava (not shown), right atrium 26, and into right ventricle 28. RV lead 18 may be used to deliver RV pacing to heart 12. Left ventricular (LV) lead 20 extends through one or more veins, the vena cava, right atrium 26, and into the coronary sinus 30 to a region adjacent to the free wall of left ventricle 32 of heart 12. LV lead 20 may be used to deliver LV pacing to heart 12. Right atrial (RA) lead 22 extends through one or more veins and the vena cava, and into the right atrium 26 of heart 12. RA lead 22 may be used to deliver RA pacing to heart 12.

In some examples, system 10B may additionally or alternatively include one or more leads or lead segments (not shown in FIG. 2) that deploy one or more electrodes within the vena cava or other vein, or within or near the aorta. Furthermore, in another example, system 10B may additionally or alternatively include one or more additional intravenous or extravascular leads or lead segments that deploy one or more electrodes epicardially, e.g., near an epicardial fat pad, or proximate to the vagus nerve. In other examples, system 10B need not include one of ventricular leads 18 and 20.

IMD 16B may sense electrical signals attendant to the depolarization and repolarization of heart 12 via electrodes (described in further detail with respect to FIG. 4) coupled to at least one of the leads 18, 20, 22. In some examples, IMD 16B provides pacing pulses to heart 12 based on the electrical signals sensed within heart 12. The configurations of electrodes used by IMD 16B for sensing and pacing may be unipolar or bipolar.

IMD 16B may also provide neurostimulation therapy, defibrillation therapy and/or cardioversion therapy via electrodes located on at least one of the leads 18, 20, 22. For example, IMD 16B may deliver defibrillation therapy to heart 12 in the form of electrical pulses upon detecting ventricular fibrillation of ventricles 28 and 32. In some examples, IMD 16B may be programmed to deliver a progression of therapies, e.g., pulses with increasing energy levels, until a fibrillation of heart 12 is stopped. As another example, IMD 16B may deliver cardioversion or ATP in response to detecting ventricular tachycardia, such as tachycardia of ventricles 28 and 32.

As described above with respect to IMD 16A of FIG. 1, programmer 24 may also be used to communicate with IMD 16B. In addition to the functions described with respect to IMD 16A of FIG. 1, a user may use programmer 24 to retrieve information from IMD 16B regarding the performance or integrity of leads 18, 20 and 22 and may interact with programmer 24 to program, e.g., select parameters for, any additional therapies provided by IMD 16B, such as cardioversion and/or defibrillation.

In addition to the functions described with respect to IMD 16A of FIG. 1, a user may use programmer 24 to retrieve information from IMD 16B regarding the performance or integrity of leads 18, 20 and 22 and may interact with programmer 24 to program, e.g., select parameters for, any additional therapies provided by IMD 16B, such as cardioversion and/or defibrillation.

Figure 3:
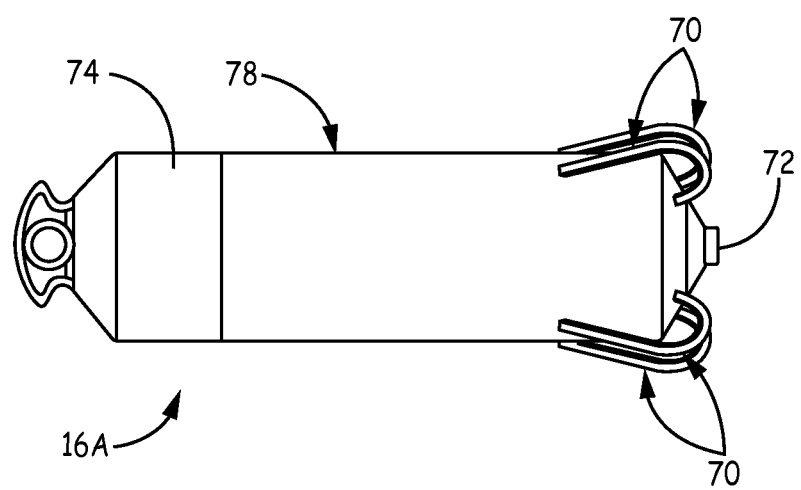
FIG. 3 illustrates the IMD of FIG. 1 in more detail

FIG. 3 is a diagram illustrating leadless IMD 16 of FIG. 1 in further detail. In the example of FIG. 3, leadless IMD 16A includes fixation mechanism 70. Fixation mechanism 70 may anchor leadless IMD 16A to a wall of heart 12. For example, fixation mechanism 70 may take the form of multiple tines that may be inserted into a wall of heart 12 to fix leadless IMD 16A at the apex of right ventricle 28. Alternatively, other structures of fixation mechanism 70, e.g., adhesive, sutures, or screws may be utilized. In some examples, fixation mechanism is conductive and may be used as an electrode, e.g., to deliver therapeutic electrical signals to heart 12 and/or sense intrinsic depolarizations of heart 12.

Leadless IMD 16A may also include electrodes 72 and 74 at a tip of outer housing 78. Electrodes 72 and 74 may be used to deliver therapeutic electrical signals to heart 12 and/or sense intrinsic depolarizations of heart 12. Electrodes 72 and 74 may be formed integrally with an outer surface of hermetically-sealed housing 78 of IMD 16A or otherwise coupled to housing 78. In this manner, electrodes 72 and 74 may be referred to as housing electrodes. In some examples, housing electrodes 72 and 74 are defined by uninsulated portions of an outward facing portion of housing 78 of IMD 16A. Other division between insulated and uninsulated portions of housing 78 may be employed to define a different number or configuration of housing electrodes. For example, in an alternative configuration, IMD 16A may include a single housing electrode that comprises substantially all of housing 78, and may be used in combination with an electrode formed by fixation mechanism 70 for sensing and/or delivery of therapy.

Figure 4:
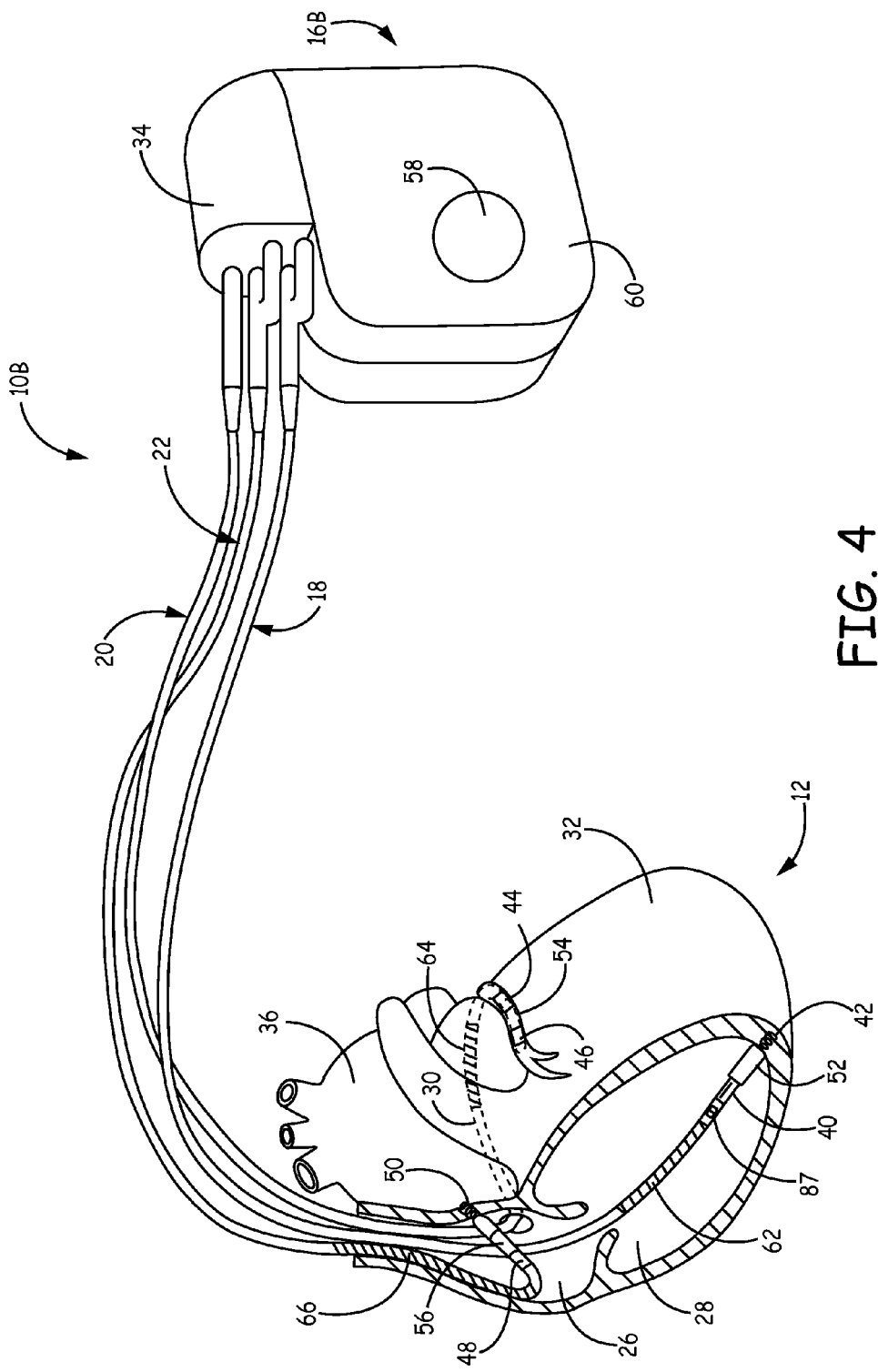
FIG. 4 illustrates the IMD of FIG. 2 in more detail

FIG. 4 is a diagram illustrating IMD 16B and leads 18, 20, 22 of therapy system 10B of FIG. 2 in greater detail. Leads 18, 20, 22 may be electrically coupled to a signal generator and a sensing module of IMD 16B via connector block 34. In some examples, proximal ends of leads 18, 20, 22 may include electrical contacts that electrically couple to respective electrical contacts within connector block 34 of IMD 16B. In some examples, a single connector, e.g., an IS-4 or DF-4 connector, may connect multiple electrical contacts to connector block 34. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in left ventricle 32 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44, and 48 may take the form of ring electrodes, and electrodes 42, 46, and 50 may take the form of extendable helix tip electrodes mounted retractably within insulative electrode heads 52, 54, and 56, respectively. In some examples, one or more of electrodes 42, 46, and 50 may take the form of pre-exposed helix tip electrodes. In other examples, one or more of electrodes 42, 46, and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64, and 66 may be electrically coupled to a respective one of the coiled conductors within the lead body of its associated lead 18, 20, 22, and thereby coupled to respective ones of the electrical contacts on the proximal end of leads 18, 20, 22.

In some examples, as illustrated in FIG. 4, IMD 16B includes one or more housing electrodes, such as housing electrode 58, which may be formed integrally with an outer surface of hermetically-sealed housing 60 of IMD 16B or otherwise coupled to housing 60. In some examples, housing electrode 58 is defined by an uninsulated portion of an outward facing portion of housing 60 of IMD 16B. Other division between insulated and uninsulated portions of housing 60 may be employed to define two or more housing electrodes. In some examples, housing electrode 58 comprises substantially all of housing 60.

IMD 16B may sense electrical signals attendant to the depolarization and repolarization of heart 12 via electrodes 40, 42, 44, 46, 48, 50, 58, 62, 64, and 66. The electrical signals are conducted to IMD 16B from the electrodes via conductors within the respective leads 18, 20, 22 or, in the case of housing electrode 58, a conductor coupled to housing electrode 58. IMD 16B may sense such electrical signals via any bipolar combination of electrodes 40, 42, 44, 46, 48, 50, 58, 62, 64, and 66. Furthermore, any of the electrodes 40, 42, 44, 46, 48, 50, 58, 62, 64, and 66 may be used for unipolar sensing in combination with housing electrode 58.

In some examples, IMD 16B delivers pacing pulses via bipolar combinations of electrodes 40, 42, 44, 46, 48 and 50 to produce depolarization of cardiac tissue of heart 12. In some examples, IMD 16B delivers pacing pulses via any of electrodes 40, 42, 44, 46, 48 and 50 in combination with housing electrode 58 in a unipolar configuration.

Furthermore, IMD 16B may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

The configuration of the systems illustrated in FIGS. 1-4 are merely exemplary. In other examples, a system may include percutaneous leads, epicardial leads and/or patch electrodes instead of or in addition to the transvenous leads 18 and 22 illustrated in FIG. 2. Further, the IMD need not be implanted within patient 14. In examples in which the IMD is not implanted in a patient, the IMD may deliver defibrillation pulses and other therapies to heart 12 via percutaneous leads that extend through the skin of patient 14 to a variety of positions within or outside of heart 12.

In addition, in other examples, a system may include any suitable number of leads coupled to IMD 16B, and each of the leads may extend to any location within or proximate to heart 12. For example, other examples of systems may include three transvenous leads located as illustrated in FIGS. 2 and 4, and an additional lead located within or proximate to left atrium 36. Other examples of systems may include a single lead that extends from IMD 16B into right atrium 26 or right ventricle 28, or two leads that extend into a respective one of the right ventricle 26 and right atrium 26. Any electrodes located on these additional leads may be used in sensing and/or stimulation configurations.

Figure 5:
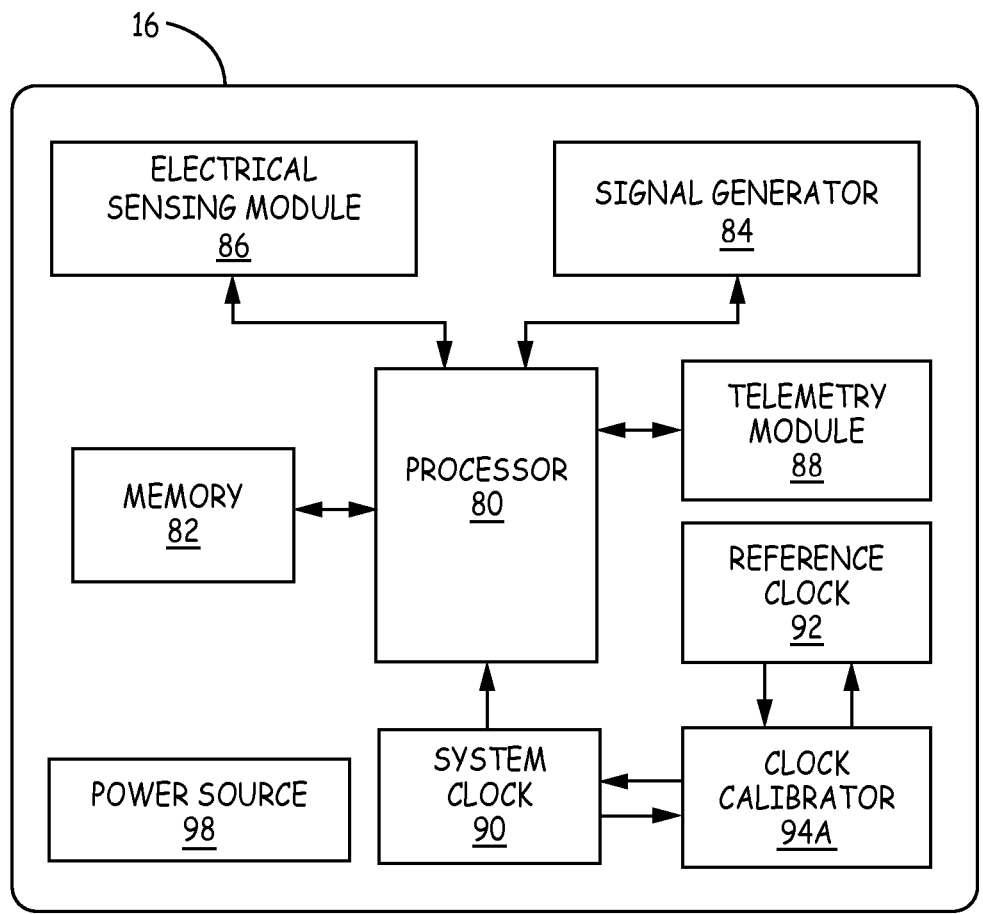
FIG. 5 is a functional block diagram illustrating an example configuration of an IMD.

FIG. 5 is a functional block diagram illustrating an example configuration of IMD 16, which may be IMD 16A of FIGS. 1 and 3 or IMD 16B of FIGS. 2 and 4. In the example illustrated by FIG. 4, IMD 16 includes a processor 80, memory 82, signal generator 84, electrical sensing module 86, telemetry module 88, system clock 90, reference clock 92, clock calibrator 94A, and power source 98. Memory 82 may include computer-readable instructions that, when executed by processor 80, cause IMD 16 and processor 80 to perform various functions attributed to IMD 16 and processor 80 herein. Memory 82 may comprise a computer-readable storage medium, including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog storage media.

Figure 6:
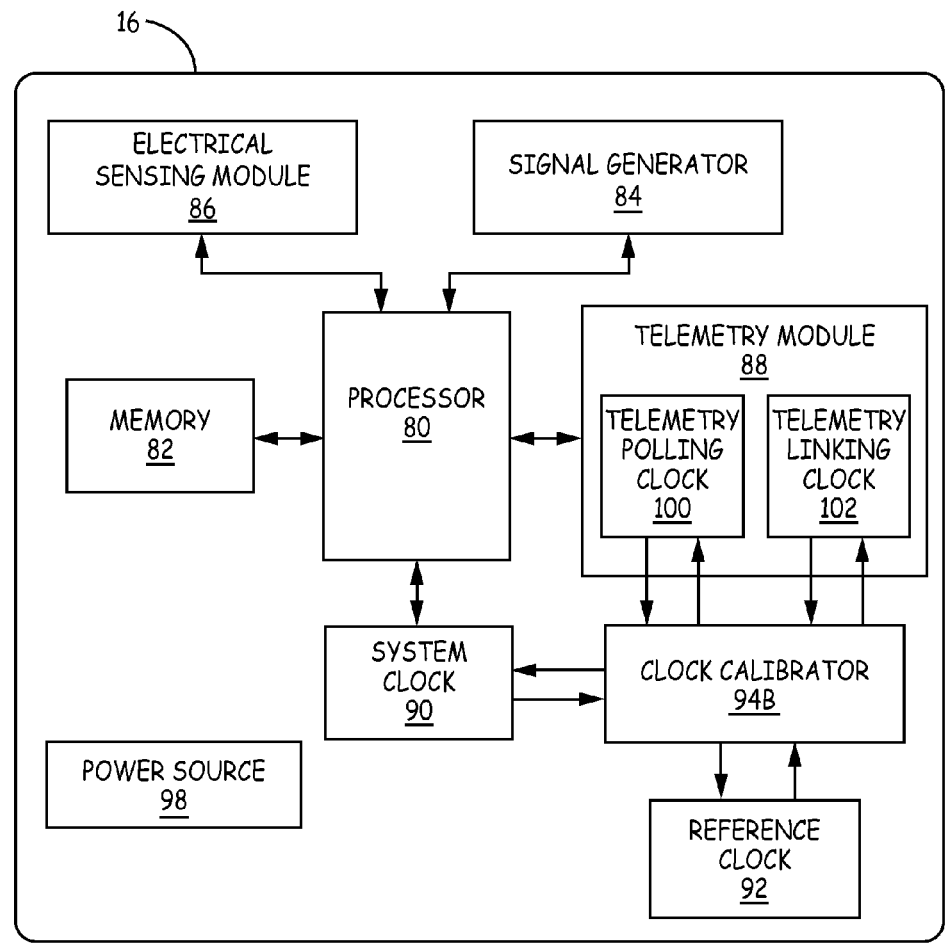
FIG. 6 is a block diagram of an example external programmer that facilitates user communication with an IMD.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 in this disclosure may be embodied as software, firmware, hardware or any combination thereof. IMD 16 also includes a sensing integrity module 90, as illustrated in FIG. 6, which may be implemented by processor 80, e.g., as a hardware component of processor 80, or a software component executed by processor 80.

In the disclosed embodiments, the operation of the device according to the invention is accomplished by the processor 80 as defined by instructions stored in memory 82. For purposes of the disclosed invention, the instruction set may correspond to the required sequence of operations as set forth in Exhibit A, attached hereto.

Processor 80 controls signal generator 84 to deliver stimulation therapy to heart 12 according to operational parameters or programs, which may be stored in memory 82. For example, processor 80 may control signal generator 84 to deliver electrical pulses with the amplitudes, pulse widths, frequency, or electrode polarities specified by the selected one or more therapy programs.

Signal generator 84, as well as electrical sensing module 86, is electrically coupled to electrodes of IMD 16 and/or leads coupled to IMD 16. In the example of leadless IMD 16A of FIG. 3, signal generator 84 and electrical sensing module 86 are coupled to electrodes 72 and 74, e.g., via conductors disposed within housing 78 of leadless IMD 16A. In examples in which fixation mechanism 70 functions as an electrode, signal generator 84 and electrical sensing module 86 may also be coupled to fixation mechanism 70, e.g., via a conductor disposed within housing 78 of leadless IMD 16A. In the example of IMD 16B of FIG. 2, signal generator 84 and electrical sensing module 86 are coupled to electrodes 40, 42, 48, 50, 56 and 62 via conductors of the respective lead 18 or 22, or, in the case of housing electrode 58, via an electrical conductor disposed within housing 60 of IMD 16B.

In the example illustrated in FIG. 4, signal generator 84 is configured to generate and deliver electrical stimulation therapy to heart 12. For example, signal generator 84 may deliver pacing, cardioversion, defibrillation, and/or neurostimulation therapy via at least a subset of the available electrodes. In some examples, signal generator 84 delivers one or more of these types of stimulation in the form of electrical pulses. In other examples, signal generator 84 may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver stimulation signals, e.g., pacing, cardioversion, defibrillation, and/or neurostimulation signals. The switch module may include a switch array, switch matrix, multiplexer, or any other type of switching device suitable to selectively couple a signal to selected electrodes.

Electrical sensing module 86 monitors signals from at least a subset of the available electrodes in order to monitor electrical activity of heart 12. Electrical sensing module 86 may also include a switch module to select which of the available electrodes are used to sense the heart activity. In some examples, processor 80 may select the electrodes that function as sense electrodes, i.e., select the sensing configuration, via the switch module within electrical sensing module 86, e.g., by providing signals via a data/address bus.

In some examples, electrical sensing module 86 includes multiple detection channels, each of which may comprise an amplifier. Each sensing channel may detect electrical activity in respective chambers of heart 12, and may be configured to detect either R-waves or P-waves. In some examples, electrical sensing module 86 or processor 80 may include an analog-to-digital converter for digitizing the signal received from a sensing channel for electrogram (EGM) signal processing by processor 80. In response to the signals from processor 80, the switch module within electrical sensing module 86 may couple the outputs from the selected electrodes to one of the detection channels or the analog-to-digital converter.

During pacing, escape interval counters maintained by processor 80 may be reset upon sensing of R-waves and P-waves with respective detection channels of electrical sensing module 86. Signal generator 84 may include pacer output circuits that are coupled, e.g., selectively by a switching module, to any combination of the available electrodes appropriate for delivery of a bipolar or unipolar pacing pulse to one or more of the chambers of heart 12. Processor 80 may control signal generator 84 to deliver a pacing pulse to a chamber upon expiration of an escape interval. Processor 80 may reset the escape interval counters upon the generation of pacing pulses by signal generator 84, or detection of an intrinsic depolarization in a chamber, and thereby control the basic timing of cardiac pacing functions. The escape interval counters may include P-P, V-V, RV-LV, A-V, A-RV, or A-LV interval counters, as examples. The value of the count present in the escape interval counters when reset by sensed R-waves and P-waves may be used by processor 80 to measure the durations of R-R intervals, P-P intervals, P-R intervals and R-P intervals. Processor 80 may use the count in the interval counters to detect heart rate, such as an atrial rate or ventricular rate.

The processor 80 also stores records of the following values in memory: a) cumulative lifetime brady pace counter; b) cumulative lifetime brady sense counter; c) programmed ventricular amplitude; and d) programmed ventricular pulse width. These values are used to determine the estimated remaining life of the pacemaker as described below.

Telemetry module 88 includes any suitable hardware, firmware, software or any combination thereof for communicating with another device, such as programmer 24 (FIGS. 1 and 2). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and receive downlinked data from programmer 24 via an address/data bus. In some examples, telemetry module 88 may provide received data to processor 80 via a multiplexer.

The clocking system of IMD 16 includes system clock 90, reference clock 92, and clock calibrator 94A. Each of the clocks described herein comprise oscillators that may operate at different frequencies with different accuracies and different power requirements. IMD 16 may require an extremely small housing form factor, especially in the case of leadless IMD 16A of FIGS. 1 and 3. For example, leadless IMD 16 may have a form factor of less than 1 cubic centimeter. Due to the small form factor requirements, IMD 16 may only be able to accommodate a small battery canister such that current drain within IMD 16 must by extremely low. One aspect of reducing power in IMD 16 is to minimize current drain by the clocking system.

A detailed description of the use of the clocking system to reduce power consumption is set forth in US Patent Publication No. US 20120109259 A1 incorporated herein by reference in its entirety FIG. 6 is a functional block diagram of an example configuration of programmer 24. As shown in FIG. 12, programmer 24 includes processor 140, memory 142, user interface 144, telemetry module 146, and power source 148. Programmer 24 may be a dedicated hardware device with dedicated software for programming of IMD 16. Alternatively, programmer 24 may be an off-the-shelf computing device running an application that enables programmer 24 to program IMD 16. In other examples, programmer 24 may be used to program IMD 16 of FIG. 7 in a substantially similar manner as IMD 16 of FIG. 6.

A user may use programmer 24 to select therapy programs (e.g., sets of stimulation parameters), generate new therapy programs, or modify therapy programs for IMD 16. The clinician may interact with programmer 24 via user interface 144, which may include a display to present a graphical user interface to a user, and a keypad or another mechanism for receiving input from a user.

Processor 140 can take the form one or more microprocessors, DSPs, ASICs, FPGAs, programmable logic circuitry, or the like, and the functions attributed to processor 140 in this disclosure may be embodied as hardware, firmware, software or any combination thereof. Memory 142 may store instructions and information that cause processor 140 to provide the functionality ascribed to programmer 24 in this disclosure. Memory 142 may include any fixed or removable magnetic, optical, or electrical media, such as RAM, ROM, CD-ROM, hard or floppy magnetic disks, EEPROM, or the like. Memory 142 may also include a removable memory portion that may be used to provide memory updates or increases in memory capacities. A removable memory may also allow patient data to be easily transferred to another computing device, or to be removed before programmer 24 is used to program therapy for another patient. Memory 142 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 146, which may be coupled to an internal antenna or an external antenna. An external antenna that is coupled to programmer 24 may correspond to the programming head that may be placed over heart 12, as described above with reference to FIG. 1. Telemetry module 146 may be similar to telemetry module 88 of IMD 16 (FIG. 6).

Telemetry module 146 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

Figure 7:
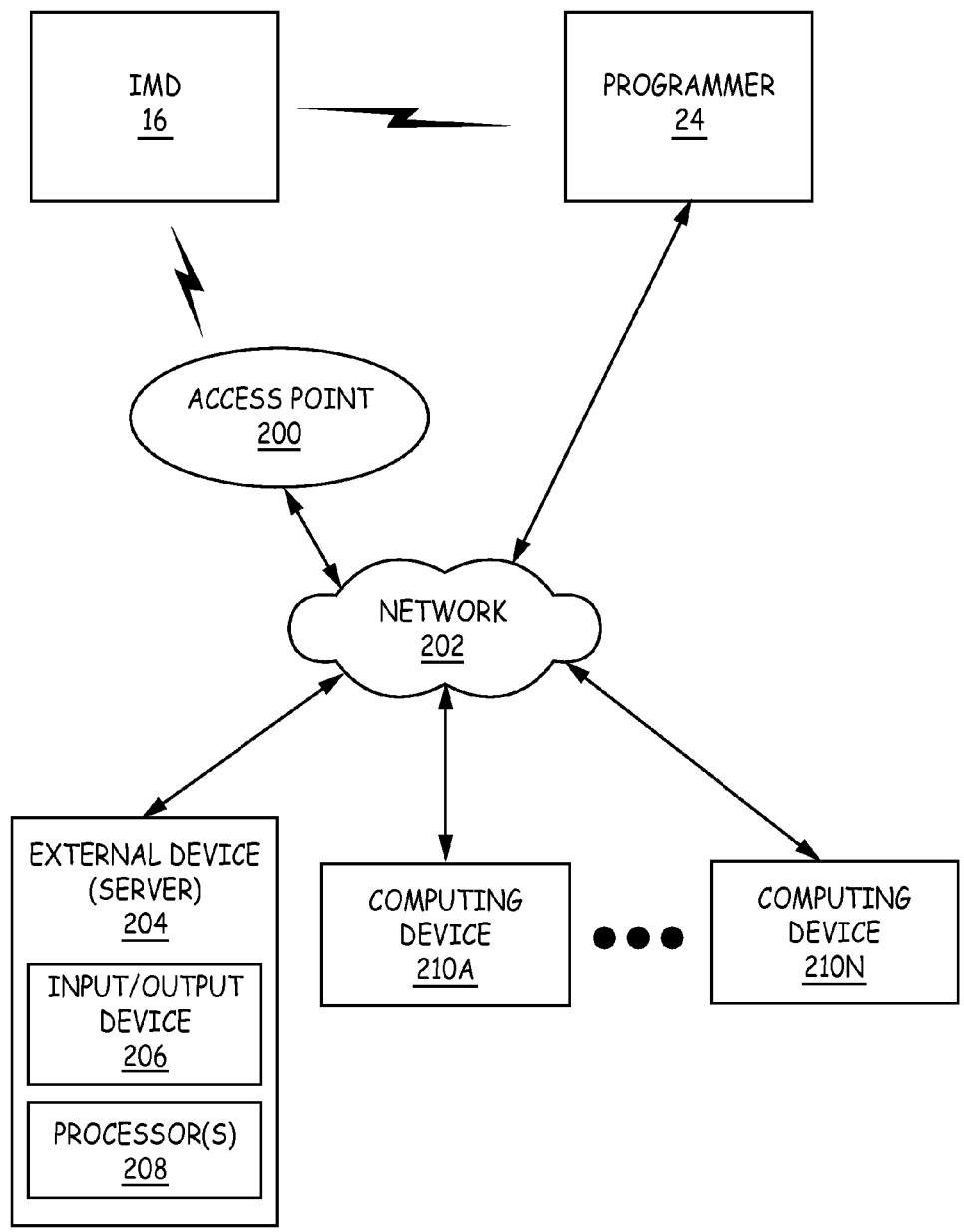
FIG. 7 is a block diagram illustrating an example system that includes an external device, such as a server, and one or more computing devices that are coupled to an IMD and programmer via a network.

FIG. 7 is a block diagram illustrating an example system that includes an external device, such as a server 204, and one or more computing devices 210A-210N, that are coupled to the IMD 16 and programmer 24 (shown in FIGS. 1 and 2) via a network 202. In other examples, the system of FIG. 13 may include IMD 116 of FIG. 7 in a substantially similar manner as IMD 16 of FIG. 6.

In this example, IMD 16 may use its telemetry module 88 to communicate with programmer 24 via a first wireless connection, and to communication with an access point 200 via a second wireless connection. In the example of FIG. 13, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described herein.

Access point 200 may comprise a device that connects to network 202 via any of a variety of connections, such as telephone dial-up, digital subscriber line (DSL), or cable modem connections. In other examples, access point 200 may be coupled to network 202 through different forms of connections, including wired or wireless connections. In some examples, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16. In some examples, server 204 or computing devices 210 may control or perform any of the various functions or operations described herein.

In some cases, server 204 may be configured to provide a secure storage site for data that has been collected from IMD 16 and/or programmer 24. Network 202 may comprise a local area network, wide area network, or global network, such as the Internet. In some cases, programmer 24 or server 206 may assemble data in web pages or other documents for viewing by trained professionals, such as clinicians, via viewing terminals associated with computing devices 210A-210N. The illustrated system of FIG. 13 may be implemented, in some aspects, with general network technology and functionality similar to that provided by the Medtronic CareLink® Network developed by Medtronic, Inc., of Minneapolis, Minn.

In one or more examples, the functions described above may be implemented in hardware, software, firmware, or any combination thereof. If implemented in software, the functions may be stored on or transmitted over as one or more instructions or code on a computer-readable medium. Computer-readable media may include computer data storage media or communication media including any medium that facilitates transfer of a computer program from one place to another. Data storage media may be any available media that can be accessed by one or more computers or one or more processors to retrieve instructions, code and/or data structures for implementation of the techniques described in this disclosure. By way of example, and not limitation, such computer-readable media can comprise RAM, ROM, EEPROM, CD-ROM or other optical disk storage, magnetic disk storage, or other magnetic storage devices, flash memory, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The code may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements.

For purposes of understanding the invention the following definitions will be helpful:

BOS—Beginning of Service

When an individual IPG is first released by the manufacturer as fit for placing on the market.

EOS—End of Service

When the Prolonged Service Period (PSP) has elapsed and performance to design specifications cannot be assured.

PSP—Prolonged Service Period

Period beyond the Recommended Replacement Time (RRT) during which the IPG continues to function as defined by the manufacturer to prolong basic bradyarrhythmia pacing.

PSL—Projected Service Life

Period from the implantation of the IPG to the Recommended Replacement Time (RRT) under defined conditions.

RRT—Recommended Replacement Time

Time when the power source indicator reaches the value set by the manufacturer of the IPG for its recommended replacement. This indicates entry into the Prolonged Service Period (PSP).

ERI—Elective Replacement Indicator

ERI is not a CENELEC definition. It is a secondary indicator which is intended to inform the user that there is less than 90 days of device service remaining.

Pre-RRT—Pre-Recommended Replacement Time

Pre-RRT is not a CENELEC definition, and it is not shown to the user. It is an indicator that the battery voltage is transitioning from the first plateau to the second plateau.

The occurrences of these events are stored in memory 82 and may be communicated to the user by means of telemetry to an associated device such as the programmer of FIG. 6 as described above. Occurrence of these events may also be communicated remotely using the system of FIG. 7 as described above The inter-relation of the above-defined defined events is illustrated in FIG. 8.

The times of occurrences of these defined events relative to an exemplary battery discharge curve are illustrated in FIG. 9.

FIG. 10 sets forth an exemplary look-up table relating pacing pulse with, pacing pulse programmed amplitude and pacing percentage to estimated battery life (Remaining Longevity Duration Value) in days.

This look-up table will of course be different for each device in each type of device in which the invention is employed, depending on the current drain, battery capacity, battery chemistry, etc. of each device type.

As an additional option, the static current drain for each individual device of a given type could be measured at production and the corresponding look up table for that device could be individually calculated and then written it to flash memory in the device. This would allow the longevity for each individual device to be maximized based on its own unique current drain.

Additionally, while the look-up table of FIG. 10 is based upon amplitude, pulse width and percentage of pacing, in alternative embodiments, additional factors such as pacing impedance could also be employed to provide a more accurate prediction of battery life.

Operation of the device generally according to the invention is according to the following set of rules as set forth below. These rules may be embodied as a corresponding instruction set stored in memory 82, executed by processor 80.

RRT Indicator

The device records the time/date that RRT occurred. Once a number of consecutive daily battery measurements are at or below a Pre-RRT voltage trip threshold as discussed below, a configurable delay timer is started as indicated at "A" below. The RRT indicator is set once that timer expires or the battery voltage become less than or equal to a RRT voltage trip threshold for a programmable number of consecutive days.

More specifically, the device sets the RRT indicator and records the Real Time Clock as a RRT Battery Voltage Detected Timestamp the first time either of the following conditions occurs:

A. Remaining Longevity Duration determined as discussed below minus the number of days since Pre-RRT Battery Voltage was detected is <=180 days.

B. Three (3) consecutive daily Battery Voltage Measurements are less than or equal to Low Battery Voltage RRT Threshold where Holter Mode was not active during any of the 3 days.

Pre-RRT Indicator

The first time three (3) consecutive daily Battery Voltage Measurements are less than or equal to a Pre-RRT voltage trip threshold where Holter Mode was not active during any of the 3 days, the device sets a Pre-RRT Battery Voltage Detected flag and records the Real Time Clock in a Pre-RRT Battery Voltage Detected Timestamp.

ERI Indicator

The device sets the ERI indicator and record the Real Time Clock in ERI Battery Voltage Detected Timestamp the first time either of the following conditions occurs:

A. Remaining Longevity Duration calculated as discussed below minus the number of days since Pre-RRT Battery Voltage was detected is <=90 days.

B. Three (3) consecutive daily battery voltage measurements are less than or equal to Low Battery Voltage ERI Threshold where Holter Mode was not active during any of the 3 days.

EOS Indicator

The device sets the EOS indicator and record the real time clock as an EOS Battery Voltage Detected Timestamp under either of the following conditions:

A. >=120 days have elapsed since the device set the ERI indicator and a POR occurs or B. Three consecutive battery voltage measurements are less than or equal to Low Battery Voltage EOS Threshold where holter mode was not active during any of the three days.

As a result, the RRT, ERI and EOS indicators as discussed above may all be triggered responsive to a determined number of days elapsing since the Pre-RRT voltage was detected. This determined number of days since Pre-RRT was detected is based upon the Remaining Longevity Duration as initially calculated and then re-calculated as discussed below.

Remaining Longevity Duration—Initial Value

Responsive to Pre-RRT Battery Voltage being detected as above, the device:

A. Determines the pacing percentage (cumulative lifetime brady pace counter/(cumulative lifetime brady pace counter+cumulative lifetime brady sense counter)); and B. Uses the pacing percentage, Programmed Ventricular Amplitude and Programmed Ventricular Pulse Width to set the Remaining Longevity Duration in days from Pre-RRT per FIG. 10 (Remaining Longevity Duration Value)

Remaining Longevity Duration Recalculation

After Pre-RRT detected as above and before ERI has been reached, each day at midnight (prior to starting any Temporary Operation scheduled to start at midnight), if:

A. The Telemetry State is Disconnect, AND

B. The Emergency VVI Timer is not active, AND

C. No Temporary Operation is in progress,

THEN the device:

A. Determines the pacing percentage (cumulative lifetime brady pace counter/(cumulative lifetime brady pace counter+cumulative lifetime brady sense counter)), AND B. Uses the pacing percentage, Programmed Ventricular Amplitude and Programmed Ventricular Pulse Width to determine the Potential Remaining Longevity Duration per FIG. 10 in days from Pre-RRT, AND C. Resets Remaining Longevity Duration to the MIN (Potential Remaining Longevity Duration, previous Remaining Longevity Duration).

Recalculation of Remaining Device Longevity therefore can only maintain or reduce amount of time remaining before triggering of the RRT/ERI/EOS indicators. In other words, once established, Remaining Longevity Duration may be only be reduced and this reduction means that the number of days between Pre-RRT and RRT/ERI/EOS is also reduced). Therefore, it is possible that once a change in Remaining Longevity Duration is identified, the number of days since Pre-RRT may already be larger than the newly changed Remaining Longevity Duration. In this case, RRT will be triggered immediately.

Mode Change at ERI

When ERI is detected, if the device is in a pacing mode, the device will change to standard ERI settings of WI pacing at 65 bpm.

The external instrument (programmer) may re-program the parameters after the device has changed to the ERI values.

ERI Parameter Change

When ERI is detected and the programmed Brady Pacing Mode is not OOO or OVO, the device shall change the brady parameter values as follows:

A. The programmed Brady Pacing Mode shall be set to VVI

B. The programmed Brady Lower Rate shall be set to 65 BPM

C. The programmed Brady Hysteresis Enable shall be set to OFF. Hysteresis is disabled to ensure that paces are delivered at 65 BPM Various examples of the disclosure have been described. These and other examples are within the scope of the following claims.

For example, while the disclosed embodiment takes the form of a pacemaker, the invention is readily applicable to other stimulator types including implantable neuro-stimulators, and implantable cardioverters or in other implantable devices wherein battery drain may be variable over time as conditions of device use change. Further, while the invention is especially useful in the context of leadless implantable devices, it is correspondingly beneficial in the context of devices including one or more leads as discussed above.

The invention claimed is:

1. A method of determining estimated remaining longevity for an implantable stimulator, comprising:
   employing pre-calculated numbers of days for various combinations of device usage parameters to determine remaining device longevity based upon identified actual conditions of device usage;
   employing the determined longevity to change longevity indicator states in the device; and
   while between longevity state changes, monitoring to verify that the device continues to operate according to the identified conditions of device usage and adjusting the determined longevity if conditions of use change significantly.

2. A method according to claim 1 wherein the indicator states correspond to one or more of Recommended Replacement Time (RRT), Elective Replacement Indicator (ERI) or End of Service (EOS).

3. A method of determining estimated remaining longevity for an implantable stimulator, comprising:
   employing pre-calculated numbers of days for various combinations of device usage parameters to determine remaining device longevity based upon identified actual conditions of device usage;
   employing the determined longevity to change longevity indicator states in the device;
   while between longevity state changes, monitoring to verify that the device continues to operate according to the identified conditions of device usage and adjusting the determined longevity if conditions of use change significantly; and
   wherein the device usage parameters comprise pacing pulse amplitude, pacing pulse duration and percentage of pacing.

4. A method according to claim 3 wherein the determination of remaining device longevity is repeated at defined intervals after the initial determination of remaining device longevity.

5. A method according to claim 3 wherein repeating the determination of remaining device longevity can only result in the determined remaining device longevity staying the same or being reduced.

6. A method according to claim 3 wherein the indicator states correspond to one or more of Recommended Replacement Time (RRT), Elective Replacement Indicator (ERI) or End of Service (EOS).

7. A method of determining estimated remaining longevity for an implantable stimulator, comprising:
   employing pre-calculated numbers of days for various combinations of device usage parameters to determine remaining device longevity based upon identified actual conditions of device usage;
   employing the determined longevity to change longevity indicator states in the device;
   while between longevity state changes, monitoring to verify that the device continues to operate according to the identified conditions of device usage and adjusting the determined longevity if conditions of use change significantly; and
   wherein the determination of remaining device longevity is performed initially in response to device battery voltage falling below a defined voltage threshold.

8. A method according to claim 7 wherein the determined remaining device longevity comprises a first defined time period following the device battery voltage falling below the defined voltage threshold.

9. A method according to claim 8 wherein changing a longevity indicator state in the device occurs in response to expiration of a second time periods following device battery voltage falling below the defined voltage threshold and wherein the second time periods is determined based upon the determined remaining device longevity.

10. A method according to claim 7 wherein the determination of remaining device longevity is repeated at defined intervals after the initial determination of remaining device longevity.

11. A method according to claim 10 wherein repeating the determination of remaining device longevity can only result in the determined remaining device longevity staying the same or being reduced.

12. An apparatus for determining estimated remaining longevity for an implantable stimulator, comprising:
   means for employing pre-calculated numbers of days for various combinations of device usage parameters to determine remaining device longevity based upon identified actual conditions of device usage;
   means for employing the determined longevity to change longevity indicator states in the device; and
   means for monitoring while between longevity state changes to verify that the device continues to operate according to the identified conditions of device usage and to adjust the determined longevity if conditions of use change significantly.

13. An apparatus according to claim 12 wherein the indicator states correspond to one or more of Recommended Replacement Time (RRT), Elective Replacement Indicator (ERI) or End of Service (EOS).

14. An apparatus for determining estimated remaining longevity for an implantable stimulator, comprising:
   means for employing pre-calculated numbers of days for various combinations of device usage parameters to determine remaining device longevity based upon identified actual conditions of device usage;

means for employing the determined longevity to change longevity indicator states in the device;

means for monitoring while between longevity state changes to verify that the device continues to operate according to the identified conditions of device usage and to adjust the determined longevity if conditions of use change significantly; and wherein the device usage parameters comprise pacing pulse amplitude, pacing pulse duration and percentage of pacing.

15. An apparatus according to claim 14 wherein the determination of remaining device longevity is repeated at defined intervals after the initial determination of remaining device longevity.

16. An apparatus according to claim 14 wherein repeating the determination of remaining device longevity can only result in the determined remaining device longevity staying the same or being reduced.

17. An apparatus according to claim 14 wherein the indicator states correspond to one or more of Recommended Replacement Time (RRT), Elective Replacement Indicator (ERI) or End of Service (EOS).

18. An apparatus for determining estimated remaining longevity for an implantable stimulator, comprising:

means for employing pre-calculated numbers of days for various combinations of device usage parameters to determine remaining device longevity based upon identified actual conditions of device usage;

means for employing the determined longevity to change longevity indicator states in the device;

means for monitoring while between longevity state changes to verify that the device continues to operate according to the identified conditions of device usage and to adjust the determined longevity if conditions of use change significantly; and wherein the determination of remaining device longevity is performed initially in response to device battery voltage falling below a defined voltage threshold.

19. An apparatus according to claim 18 wherein the determined remaining device longevity comprises a first defined time period following the device battery voltage falling below the defined voltage threshold.

20. An apparatus according to claim 19 wherein changing a longevity indicator state in the device occurs in response to expiration of a second time period following device battery voltage falling below the defined voltage threshold and wherein the second time periods is determined based upon the determined remaining device longevity.

21. An apparatus according to claim 18 wherein the determination of remaining device longevity is repeated at defined intervals after the initial determination of remaining device longevity.

22. An apparatus according to claim 21 wherein repeating the determination of remaining device longevity can only result in the determined remaining device longevity staying the same or being reduced.

23. A non-transitory programming medium comprising instructions for determining estimated remaining longevity for an implantable stimulator, comprising:

instructions for employing pre-calculated numbers of days for various combinations of device usage parameters to determine remaining device longevity based upon identified actual conditions of device usage;

instructions for employing the determined longevity to change longevity indicator states in the device; and instructions for monitoring while between longevity state changes to verify that the device continues to operate according to the identified conditions of device usage and to adjust the determined longevity if conditions of use change significantly.

24. A medium according to claim 23 wherein the indicator states correspond to one or more of Recommended Replacement Time (RRT), Elective Replacement Indicator (ERI) or End of Service (EOS).

25. A medium according to claim 23, wherein the device usage parameters comprise pacing pulse amplitude, pacing pulse duration and percentage of pacing.

* * * * *